(12) United States Patent
Zheng et al.

(10) Patent No.: US 10,194,775 B2
(45) Date of Patent: Feb. 5, 2019

(54) HAND DRYER (71) Applicant: Zhejiang Aike Appliances Co., Ltd., Taizhou (CN)

(72) Inventors: Fuming Zheng, Taizhou (CN); Junxiang Wang, Taizhou (CN)

(73) Assignee: ZHEJIANG AIKE APPLIANCES CO., LTD., Taizhou (CN)

( * ) Notice: Subject to any disclaimer, the term of this patent is extended or adjusted under 35 U.S.C. 154(b) by 297 days.

(21) Appl. No.: 15/194,581

(22) Filed: Jun. 28, 2016

(65) Prior Publication Data
US 2017/0000300 A1   Jan. 5, 2017

(30) Foreign Application Priority Data

Jun. 30, 2015  (CN) .......................... 2015 1 0382597

(51) Int. Cl.
*A47K 10/48*  (2006.01)
*A61L 9/12*  (2006.01)

(52) U.S. Cl.
CPC .............. *A47K 10/48* (2013.01); *A61L 9/122* (2013.01); *A47K 2201/02* (2013.01); *A61L 2209/111* (2013.01); *A61L 2209/13* (2013.01); *A61L 2209/14* (2013.01)

(58) Field of Classification Search
CPC .............. A47K 10/48; A47K 2201/02; A61L 2209/111; A61L 2209/13; A61L 2209/14; A61L 9/122
USPC ............................................................. 34/90
See application file for complete search history.

(56) References Cited

U.S. PATENT DOCUMENTS

| | | | | |
|---|---|---|---|---|
| 1,997,387 A | * | 4/1935 | McCord | A47K 10/48 34/202 |
| 3,766,397 A | * | 10/1973 | Rockson | A47K 10/48 250/432 R |
| 5,074,322 A | * | 12/1991 | Jaw | A47K 10/48 134/56 R |
| 5,459,944 A | * | 10/1995 | Tatsutani | A47K 10/48 34/202 |
| 6,038,786 A | * | 3/2000 | Aisenberg | A47K 10/48 34/202 |
| 6,050,000 A | * | 4/2000 | Curzon | A47K 10/48 34/202 |

(Continued)

FOREIGN PATENT DOCUMENTS

| | | | |
|---|---|---|---|
| CN | 104921646 A | * | 9/2015 |
| EP | 1839546 B1 | * | 10/2007 |

(Continued)

*Primary Examiner* — Stephen M Gravini
(74) *Attorney, Agent, or Firm* — Perkins Coie LLP (57) ABSTRACT

A hand dryer includes a housing, a core and end covers. The housing takes the shape of a hollow tube with two ends opened, having a first end and a second end. The core is disposed inside the housing, and two ends of the core are disposed correspondingly to two ends of the housing. The end covers include a first end cover and a second end cover. The first end cover and the second end cover are respectively detachably connected with the first end and the second end of the housing. The core is fixed inside the housing, a shape of a cross section of the first end cover is the same as a shape of an end surface of the first end, and a shape of a cross section of the second end cover is the same as a shape of an end surface of the second end.

12 Claims, 8 Drawing Sheets

(56) References Cited

U.S. PATENT DOCUMENTS

| | | | | |
|---|---|---|---|---|
| 6,189,230 B1* | 2/2001 | Huen | ................. | A47K 10/06 |
| | | | | 34/210 |
| 7,437,833 B2* | 10/2008 | Sato | ................. | A47K 10/48 |
| | | | | 34/90 |
| 7,555,209 B2* | 6/2009 | Pradas Diez | ......... | A47K 10/48 |
| | | | | 34/202 |
| D719,299 S * | 12/2014 | Bao | ................. | D28/54.1 |
| D719,300 S * | 12/2014 | Bao | ................. | D28/54.1 |
| 9,826,865 B2* | 11/2017 | Maruyama | ............ | G01F 23/268 |
| 2014/0208608 A1* | 7/2014 | Robert | ................. | A47K 10/48 |
| | | | | 34/523 |
| 2014/0212304 A1* | 7/2014 | Michael | ................. | F04D 25/082 |
| | | | | 417/363 |
| 2015/0328355 A1* | 11/2015 | Rubin | ................. | F24F 3/1603 |
| | | | | 422/4 |
| 2017/0000300 A1* | 1/2017 | Zheng | ................. | A47K 10/48 |

FOREIGN PATENT DOCUMENTS

| | | | |
|---|---|---|---|
| GB | 909069 | * | 10/1962 |
| GB | 2461699 | * | 1/2010 |
| JP | 2005110176 A1 | * | 10/2003 |
| WO | WO2005110176 A1 | * | 5/2005 |
| WO | WO2017022110 A1 | * | 8/2015 |

* cited by examiner

HAND DRYER

CROSS REFERENCE TO RELATED APPLICATION

This application claims priority to and incorporates by reference CN 201510382597.5 filed 2015 Jun. 30.

BACKGROUND OF THE INVENTION

Technical Field

The invention relates to a hand drying equipment and, more particularly, relates to a hand dryer.

Description of the Related Art

Hand dryers are sanitary electric appliances for drying or blowing hands in bathrooms, and are advanced and ideal sanitary fittings and equipments. The hand dryers are generally used in hotels, restaurants, scientific research institutes, hospitals, public entertainment venues and bathrooms of families. After washing their hands, people can stretch out their hands under the air outlet of an automatic hand dryer, and then the hand dryers can automatically blow out comfortable air to dry the hands immediately. People do not need to dry their hands with towels to prevent cross infection of disease.

Once an existing hand dryer is developed, the style is relatively fixed and the appearance is very simple. An existing method is to design structures independently for different appearances, which is equivalent to design a new equipment. This involves problems of product design and development, mold replacement, and the like. The product design and development cost is greatly increased, and meanwhile the product development period can be prolonged.

In addition, the existing hand dryer is generally suspended on a mounting transverse bar after the mounting transverse bar is fixed in a mounting position such as a wall. However, the hand dryer can be easily stolen as the hand dryer is generally disposed in a public place.

BRIEF SUMMARY OF THE INVENTION

To solve the problem that a housing of an existing hand dryer is hard to replace, the present invention provides a hand dryer, the production cost of the hand dryer is low, and the housing of the hand dryer can be flexibly replaced.

To achieve the objective, the present invention provides a hand dryer including a housing, a core and end covers. The housing takes the shape of a hollow tube with two ends opened, and has a first end and a second end. The core is disposed inside the housing, and two ends of the core are disposed correspondingly to two ends of the housing. The end covers include a first end cover and a second end cover, and the first end cover and the second end cover are respectively detachably connected with the first end and the second end of the housing. The core is fixed inside the housing, a shape of a cross section of the first end cover is the same as a shape of an end surface of the first end of the housing, and a shape of a cross section of the second end cover is the same as a shape of an end surface of the second end of the housing.

In one embodiment of the invention, the hand dryer may further include a mounting plate, a mounting buckle, and a groove plate, a side wall of the housing may have a mounting groove concaving inwards to the housing, the mounting buckle and the groove plate may be fixed on the mounting groove, and the mounting plate may be fixedly connected with the mounting buckle and the groove plate.

In one embodiment of the invention, the mounting plate may include a plate body, a connecting buckle, and a connecting plate, the connecting buckle and the connecting plate may be disposed at two ends of the plate body, the connecting buckle may be fixedly connected with the mounting buckle, and the connecting plate may be connected with the groove plate.

In one embodiment of the invention, the hand dryer may further include a noise reduction layer disposed on an inner surface of the housing.

In one embodiment of the invention, the core may include a core housing, an air inlet and an air outlet, the air inlet and the air outlet may be respectively disposed at two end surfaces of the core housing, the air outlet may be disposed at an end surface close to the first end cover of the core housing, and the air inlet may be disposed at an end surface close to the second end cover of the core housing.

In one embodiment of the invention, the hand dryer may further include a baffle disposed on one side of the air outlet, the baffle may have a sealed area and a grid area, and the sealed area may be disposed opposite to the air outlet.

In one embodiment of the invention, the hand dryer may further include an air inlet grid detachably disposed on one side away from the core of the first end cover.

In one embodiment of the invention, the hand dryer may further include a filtering element, disposed between the air inlet grid and the first end cover.

In one embodiment of the invention, the hand dryer may further include a display window, disposed at the first end cover, and being used for displaying the power on and operation state of the hand dryer.

In one embodiment of the invention, the hand dryer may further include a perfume diffuser, disposed on one side of the second end cover.

In one embodiment of the invention, the perfume diffuser may include a bottom cover, a window frame and a window plate, the bottom cover may be disposed on one side of the second end cover, the window frame may be mounted on one side of the bottom cover away from the second end cover, the bottom cover may have a containing groove for containing perfume, the window frame may have an opening, the window plate may be rotatably mounted at the opening, and the window plate may have a ventilation area.

In one embodiment of the invention, the perfume diffuser may further include a fan disposed on one side of the containing groove.

In one embodiment of the invention, the perfume diffuser may further include a perfume bottle and a volatilization stick, the perfume bottle may be positioned inside the containing groove, and the volatilization stick may be inserted into the perfume bottle.

In one embodiment of the invention, the window plate may have two rotating shafts, the window plate may have two first half grooves, the bottom cover may have two second half grooves, the two first half grooves may be respectively corresponding to the two second half grooves to form two shaft holes, and two rotating shafts may be rotatably inserted into the shaft holes.

In conclusion, compared with the prior art, the hand dryer in the invention has following advantages.

The housing of the hand dryer in the invention is designed into a hollow tube structure with two ends opened. The housing of the hand dryer can be made of stainless steel plates with different surface appearances in a direct punching manner or made of an aluminum alloy material in an extrusion manner. The formation process is simple, the material utilization rate is high, and meanwhile as the formation process causes no damage, the original surface of the plate can be maintained after the product is formed, and the formed housing can be smooth and attractive and needs no extra polishing or spraying. The production efficiency is high, and the production cost is relatively low. Furthermore, the first end cover and the second end cover are detachably connected with the first end and the second end of the housing, and moreover the shape of the cross section of the first end cover is the same as the shape of the end surface of the first end, and the shape of the cross section of the second end cover is the same as the shape of the end surface of the second end. When the shape of the hand dryer needs to be changed, a user only needs to change the shapes of the housing and the end covers, and other parts do not need to be redesigned, so that the product development cost can be greatly reduced, and the development period can be greatly shortened. Furthermore, the user can change the appearance of the hand dryer at will according to demands, so that the hand dryer is not only convenient to use, but also relatively low in use cost.

In addition, when being mounted, the hand dryer is fixed on the wall through a fixed connection with the mounting plate, the mounting buckle and the groove plate. After being mounted, the mounting plate and the mounting buckle can be separated only by using special tools, so that the anti-theft effect of the hand dryer is greatly improved. As the baffle is mounted, the sealed area of the baffle is disposed opposite to the air outlet, hands or other articles can be effectively prevented from stretching into the air outlet to cause danger, furthermore noise generated when the blower is rotated inside the core can be conducted out through the air outlet and can be reflected at the sealed area, and most noise can be conducted into the core again, so that the operation noise of the hand dryer can be greatly reduced. Due to the noise reduction layer disposed on the inner surface of the housing, the noise generated when the hand dryer is used can be further reduced. In addition, the hand dryer further includes the perfume diffuser, and due to the perfume diffuser, perform can be diffuse out to adjust the atmosphere of a room.

To make the above-mentioned and other purposes, features and advantages of the present invention better understood, preferred embodiments will be described in detail below in combination with the accompanying drawings.

DETAILED DESCRIPTION OF THE INVENTION

Figure 1:
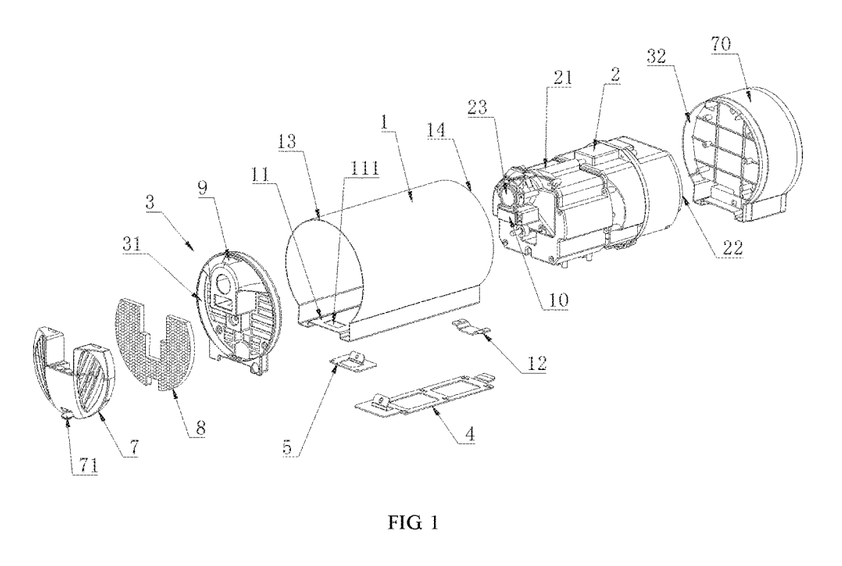
FIG. 1 is an exploded view of a hand dryer according to one embodiment of the present invention.

As shown in FIG. 1, the present invention provides a hand dryer, including a housing 1, a core 2 and end covers 3. The housing 1 takes the shape of a hollow tube with two ends opened, and has a first end 13 and a second end 14. The core 2 is disposed inside the housing 1, and two ends of the core 2 are disposed correspondingly to two ends of the housing 1. The end covers 3 include a first end cover 31 and a second end cover 32, and the first end cover 31 and the second end cover 32 are respectively detachably connected with two ends of the housing 1. The core 2 is fixed inside the housing 1. A shape of a cross section of the first end cover 31 is the same as a shape of an end surface of the first end 13 of the housing 1, and a shape of a cross section of the second end cover 32 is the same as a shape of an end surface of the second end 14 of the housing 1.

Figure 5:
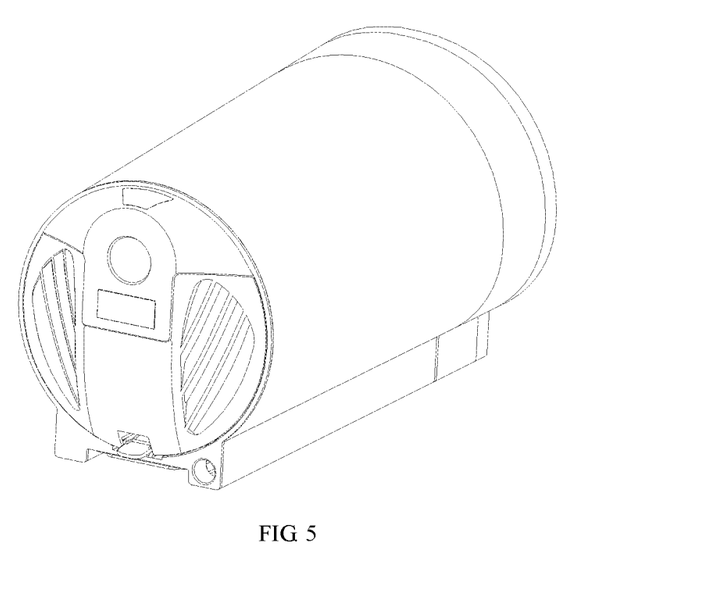

In this embodiment, the housing 1 takes the shape of a hollow straight tube. The shape of the end surface of the first end 13 of the housing 1 is the same as the shape of the end surface of the second end 14, and the shape of the end surface of the first end 13 of the housing 1 and the shape of the end surface of the second end 14 are both partial circle, as shown in FIG. 1. The partial circle is a shape that a complete circle is cut by a side wall with a mounting groove. The housing of the structure is not only attractive in appearance and simple in process, but also relatively low in production cost. However, the invention is not limited thereto. In other embodiments, the end surfaces of the first end 13 and the second end 14 of the housing 1 can take the shape of one of circle, ellipse, partial ellipse, polygon, heart, partial quincunx and other irregular shapes. Such as the end surfaces of the first end 13 and the second end 14 take the shape of polygon, or the end surface of the first end 13 takes the shape of a polygon, and the end surface of the second end 14 can take the shape of a heart, or other combinations. In addition, the housing 1 can take the shape of a non-straight tube, such as a hollow structure of a frustum (as shown in FIG. 5) or a hollow structure of a shuttle.

In this embodiment, the housing 1 is made of a stainless steel plate in a punching manner and takes the shape of the hollow straight tube. However, the invention is not limited thereto. In other embodiments, the housing 1 can be made of an aluminum alloy material in an extrusion molding manner. The plate can be formed into a hollow straight tube, the plate is high in utilization rate and simple and convenient in process, and the surface of the machined material is not damaged and has a good appearance.

The first end cover 31 and the second end cover 32 are detachably disposed at two ends of the housing 1, the shape of the cross section of the first end cover 31 is the same as the shape of the end surface of the first end 13 of the housing 1, and the shape of the cross section of the second end cover 32 is the same as the shape of the end surface of the second end 14 of the housing 1. In practical use, the housing 1 and the corresponding first end cover 31 and second end cover 32 can be replaced according to user demands (different aesthetics of users of different countries or areas) so as to replace the appearance of the hand dryer. Other components inside the hand dryer do not need to be redesigned, so that the product production cost can be greatly lowered, the production period can be greatly shortened. For the users, one core is matched with a plurality of appearances of the hand dryer, so that the hand dryer is applicable to more occasions, and the purpose of reducing the use cost can be also achieved.

As the hand dryer is generally mounted in public places such as a doorway of a toilet, an existing hand dryer is generally suspended on a mounting bar after the mounting bar is fixed in a mounting position such as a wall. Due to this mounting manner, the hand dryer can be conveniently detached by an operator, but the hand dryer can also be easily stolen. To solve the problem, the hand dryer in the embodiment includes a mounting plate 4, a mounting buckle 5 and a groove plate 12. A side wall of the housing 1 has a mounting groove 11 concaving inwards to the housing 1. The mounting buckle 5 and the groove plate 12 are fixed on the mounting groove 11. The mounting plate 4 and the mounting buckle 5 are connected and locked by virtue of screws. In the embodiment, the mounting buckle 5 is made of stainless steel. The mounting groove 11 has a mounting hole 111, the mounting buckle 5 is welded with the circumference of the mounting hole 111, and the groove plate 12 is welded with a bottom of the mounting groove 11. A thickness of the mounting plate 4 is matched with a depth of the mounting groove 11. Due to this structure, the hand dryer can be tightly fit with a mounting position, such as a wall, and the space occupied by the hand dryer can be reduced.

Figure 6:
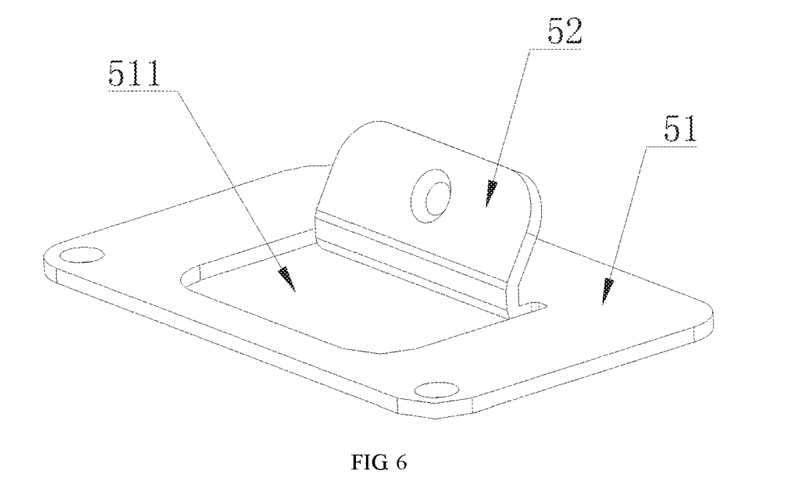
FIG. 6 is an enlarged diagram of a mounting buckle according to one embodiment of the present invention.
Figure 7:
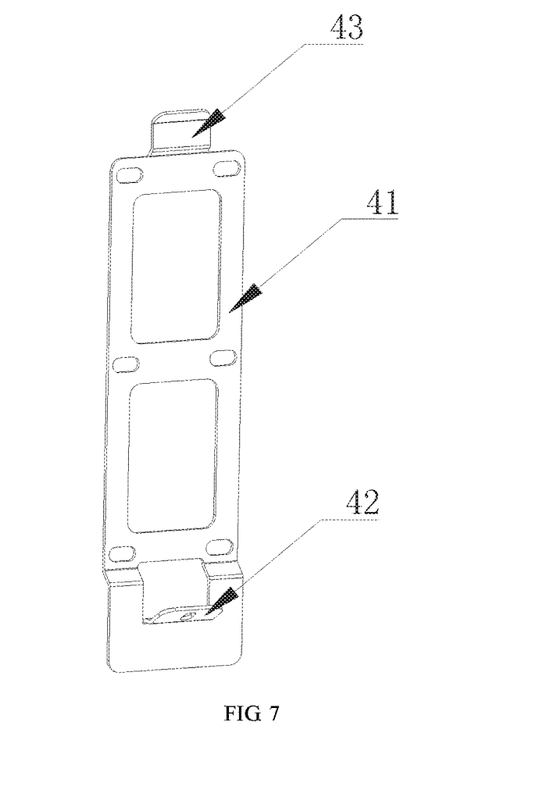
FIG. 7 is an enlarged diagram of a mounting plate according to one embodiment of the present invention.

In the embodiment, as shown in FIG. 6 and FIG. 7, the mounting buckle 5 includes a mounting buckle bottom plate 51 and a buckle plate 52. The mounting buckle bottom plate 51 has a through hole 511, the buckle plate 52 is disposed on one side of the through hole 511, and the buckle plate 52 has a first connecting hole. The mounting plate 4 includes a plate body 41, a connecting buckle 42 and a connecting plate 43, and the connecting buckle 42 and the connecting plate 43 are respectively disposed at two ends of the plate body 41. A diameter of the connecting buckle 42 is smaller than a diameter of the through hole 511. The connecting buckle 42 has a second connecting hole.

Figure 8:
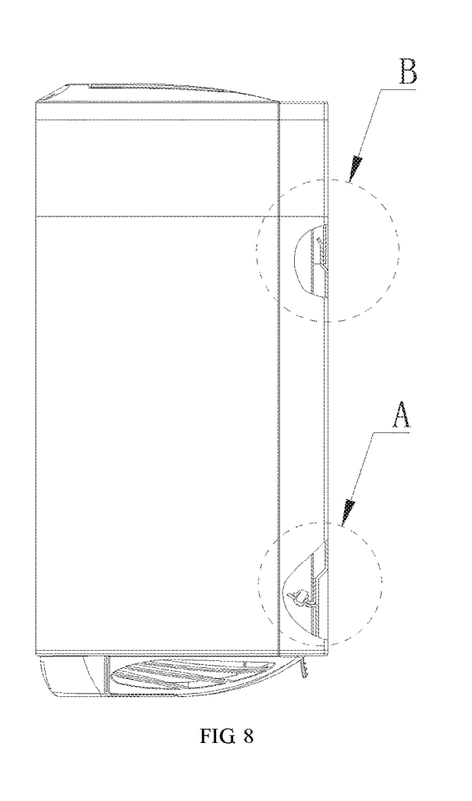
FIG. 8 is a structural diagram that the mounting buckle is connected with the mounting plate as shown in FIG. 6 and FIG. 7.
Figure 9:
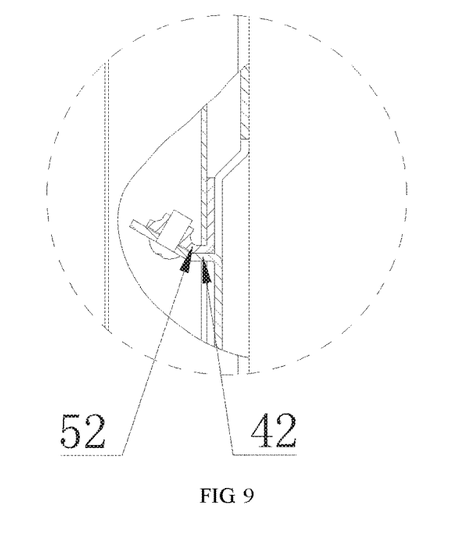
FIG. 9 is an enlarged diagram of A in FIG. 8.
Figure 10:
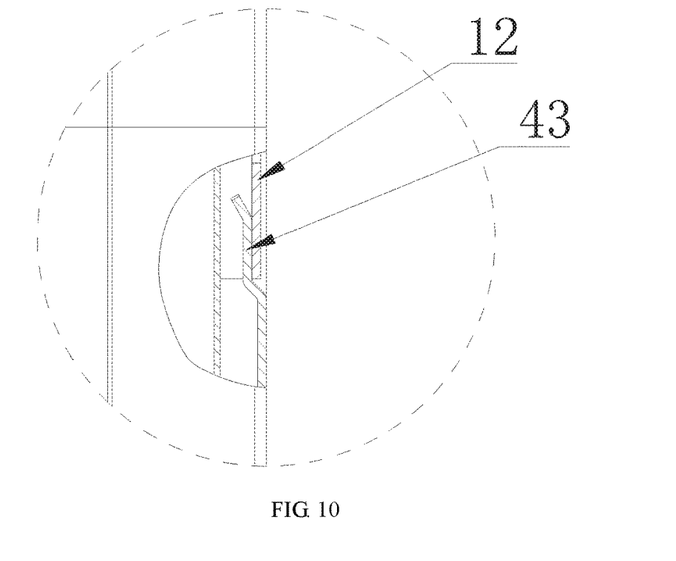
FIG. 10 is an enlarged diagram of B in FIG. 8.

As shown in FIG. 8, a specific installation is as follows. Firstly, the mounting plate 4 is fixed on a mounting position such as a wall. Secondly, the groove plate 12 disposed in the bottom of the mounting groove 11 is buckled into the connecting plate 43 of the mounting plate 4, at the same time the connecting buckle 42 penetrates through the through hole 511, and then the second connecting hole of the connecting buckle 42 faces to the first connecting hole of the buckle plate 52. The first connecting hole and the second connecting hole are connected by a connecting piece, and then the housing 1 and the mounting plate 4 of the hand dryer can be fixedly connected and can be separated only by special tools. Due to this structure, not only is the anti-theft effect of the hand dryer greatly improved, but also the mounting solidness of the hand dryer is improved. In the embodiment, the connecting piece refers to screws. However, the invention is not limited thereto.

In the embodiment, the core 2 includes a core housing 21, an air inlet 22, an air outlet 23, an air channel, a blower, a heating module and a control module (the air channel, the blower, the heating module and the control module are wrapped by the core housing 21, not shown in the FIGs). The air inlet 22 and the air outlet 23 are respectively disposed at two end surfaces of the core housing 21, the air inlet 22 is disposed at one end close to the second end cover 32 of the core housing 21, and the air outlet 23 is disposed at one end close to the first end cover 31 of the core housing 21. The blower, the heating module and the control module are all disposed inside the core housing 21, and the air channel is formed between a side wall of the core housing 21, the blower and the housing.

Figure 2:
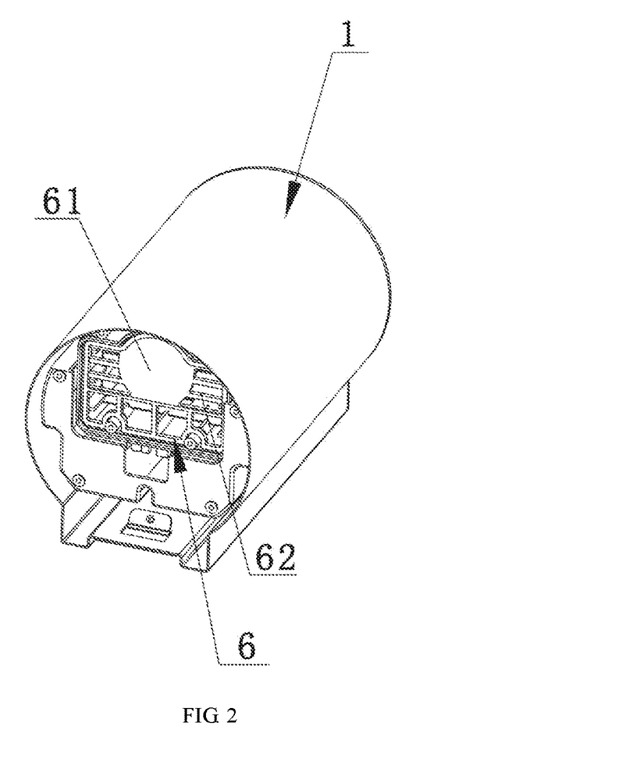
FIG. 2 is an assembling schematic diagram of a baffle and a housing.
Figure 3:
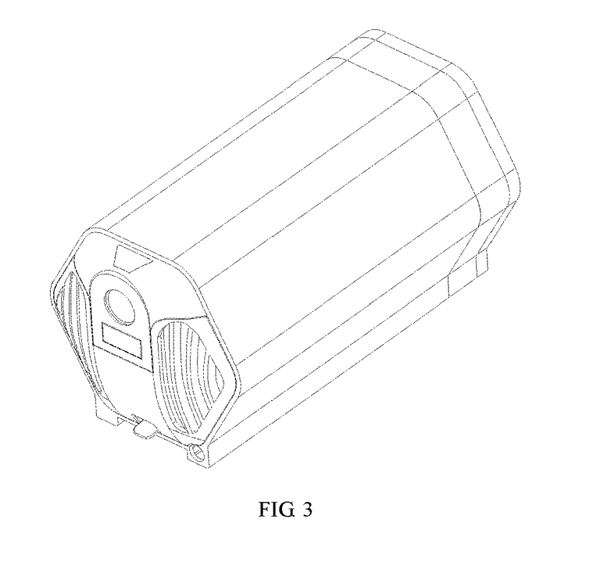
FIG. 3 to FIG. 5 are structure diagrams of hand dryers according to other embodiments of the present invention.
Figure 4:
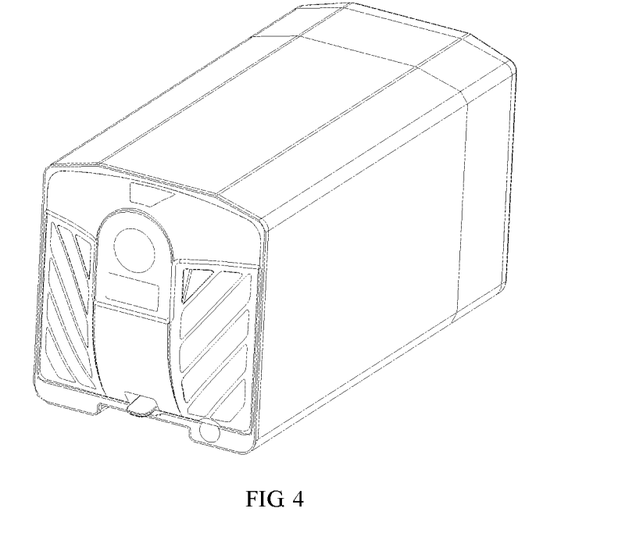

In the embodiment, the hand dryer further includes a baffle 6 disposed on one side of the air outlet 23. In the embodiment, the baffle 6 is disposed between the heating module and the air outlet 23. The baffle 6 has a sealed area 61 and a grid area 62, and the sealed area 61 is disposed opposite to the air outlet 23. Heated air can be blown out from the grid area 62 through the air outlet 23. However, the invention is not limited thereto. In other embodiments, the baffle 6 can be disposed on an outer side of an air outlet direction of the air outlet 23. Identically, when the heating module is not equipped, the baffle can be disposed on any side of the air outlet. As the sealed area 61 and the air outlet 23 are disposed opposite to each other, not only can hands or other articles be prevented from stretching into the air outlet 23 to cause accident or fault, but also noise generated by the blower can be reflected by the sealed area 61 when passing through the air outlet 23 and reaching the sealed area 61, and can be further conducted into the core 2, so that the noise generated during the hand dryer is used can be greatly reduced.

Figure 11:
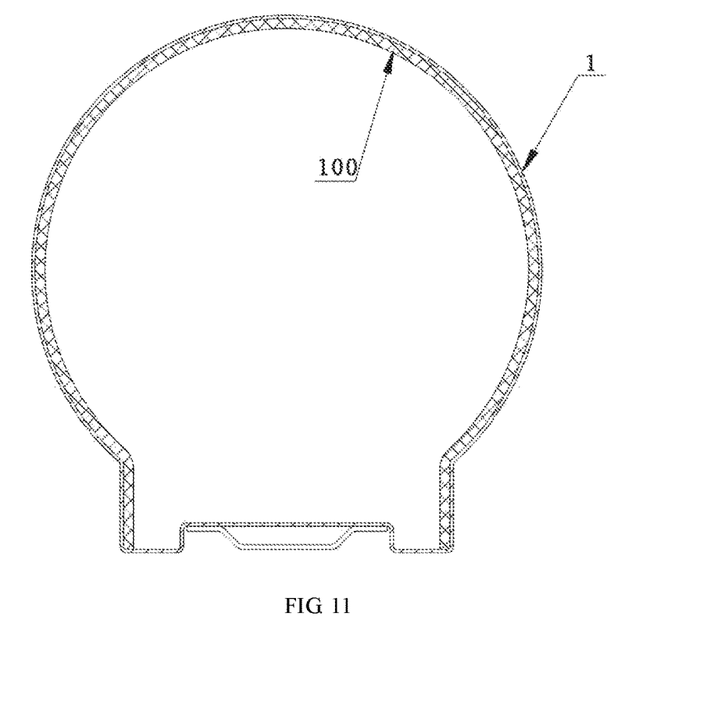
FIG. 11 is a sectional view of the mounted housing and the noise reduction layer in FIG. 1.
Figure 12:
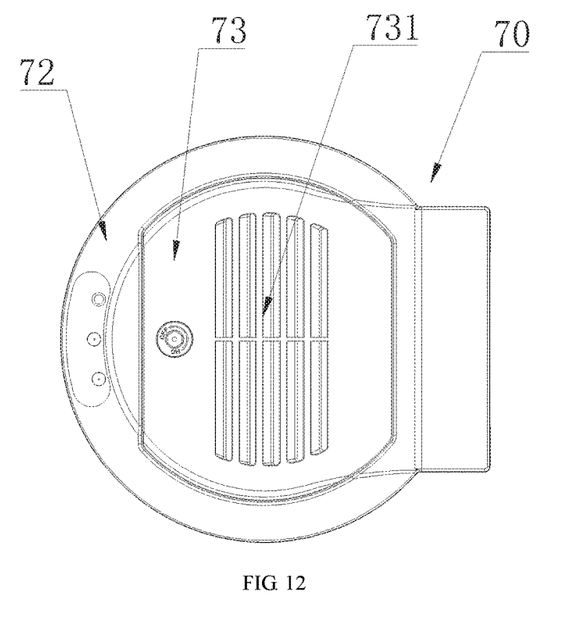
FIG. 12 is a top view of a perfume diffuser according to one embodiment of the present invention.

To further reduce the noise generated during the hand dryer is used, in the embodiment, the hand dryer further includes a noise reduction layer 100 disposed on an inner surface of the housing 1.

In the embodiment, the hand dryer further includes an air inlet grid 7, and the air inlet grid 7 is detachably disposed on one side away from the core 2 of the first end cover 31. Specifically, the air inlet grid 7 has an elastic buckle 71. The air inlet grid 7 is clamped with the first end cover 31 through the elastic buckle 71. However, the invention is not limited thereto.

The air inlet grid 7 is disposed on one side of the air outlet 23, and air can be fed into the air channel between the housing 1 and the core housing 21 through the air inlet grid 7. Under the action of the blower, air can be fed into the core 2 through the air inlet 22 disposed correspondingly to the second end cover 32, and is fed into the heating module and the baffle 6 along the air channel between the core housing 21 and the blower, and is finally blown out through the air outlet 23. In practical use, the hand dryer is generally mounted in a manner of the first end cover 31 facing downwards and the second end cover 32 facing upwards. By mounting the air grid 7 corresponding to the air outlet 23, after the hand dryer is mounted, external moisture and foreign matter cannot easily feed into the hand dryer through the air inlet grid 7, so that not only is a very high waterproof grade achieved, but also the function of expelling foreign matter can be achieved. If the air inlet grid 7 is disposed corresponding to the air inlet 22, substances such as moisture can be easily fed into the hand dryer under the action of gravity.

In the embodiment, the hand dryer further includes a filtering element 8, and the filtering element 8 is disposed between the air inlet grid 7 and the first end cover 31. In the embodiment, the filtering element 8 refers to HEPA filter. Air entering the air inlet 22 is firstly filtered by the air inlet grid 7 to remove large-size foreign matter, is further filtered by the filtering element 8 to remove large particles in the air, and is then fed into the air channel and the blower. Due to the air inlet grid 7 and the filtering element 8, not only is foreign matter effectively prevented from blocking the air channel and the blower, but also the cleanliness of the air at the air outlet 23 is greatly improved, and thus the cleanliness of user's dry hands can be improved. Furthermore, the air inlet grid 7 is engaged with the first end cover 31, components such as switches and fixing screws on the first end cover 31 can be hidden, and thus the product can be relatively more smooth and attractive in shape.

In one embodiment of the present invention, the hand dryer further includes a display window 9 and a sensor 10. The display window 9 is disposed on the first end cover 31, and the display window 9 is used for displaying power on and operation state of the hand dryer. The sensor 10 is a infrared sensor. The infrared sensor senses users' hands so as to power on the hand dryer.

Referring to FIG. 1, in one embodiment of the present invention, the hand dryer further includes a perfume diffuser 70 disposed on one side of the second end cover 32. As the hand dryer is generally mounted in a room such as a toilet or a bathroom, perfume can be diffused from the perfume diffuser 70 to adjust an atmosphere in the room.

As shown in FIG. 12 to FIG. 15, the perfume diffuser 70 includes a bottom cover 71, a window frame 72 and a window plate 73. The bottom cover 71 is disposed on one side of the second end cover 32. In the embodiment, the bottom cover 71 and the second end cover 32 are of an integrated structure, the structure is simple, and the manufacture process is easy, however, the invention is not limited thereto. The bottom cover 71 and the second end cover 32 can be also of a split structure, and the bottom cover 71 and the second end cover 32 are connected in the manner of adhesion, engaging, locking and the like.

The bottom cover 71 has a containing groove 701 for containing perfume. The window frame 72 is mounted on one side away from the second end cover 32 of the bottom cover 71. The window frame 72 has an opening 702, the window plate 73 is rotatably mounted at the opening 702, and the opening 702 can be opened or closed by rotating the window plate 73, so that perfume can be positioned into the containing groove 701 through the opening 702 or can be taken out from the containing groove 701 through the opening 702. The window plate 73 has a ventilation area 731, so that the air inside the perfume diffuser 70 can be communicated with the outside of the perfume diffuser 70. After the perfume is positioned into the containing groove 701, the fragrance can be diffused through the ventilation area 731. In the embodiment, the ventilation area 731 refers to a grid area. Due to the ventilation area 731, on one side, normal diffusion of the fragrance can be ensured, and on the other side, foreign matter can be prevented from falling into the containing groove 701.

Figure 13:
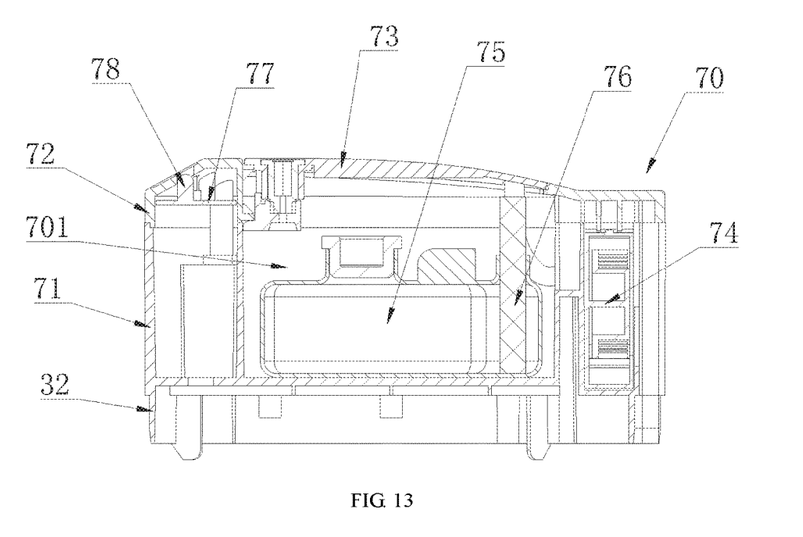
FIG. 13 is a sectional view of the perfume diffuser according to one embodiment of the present invention.
Figure 14:
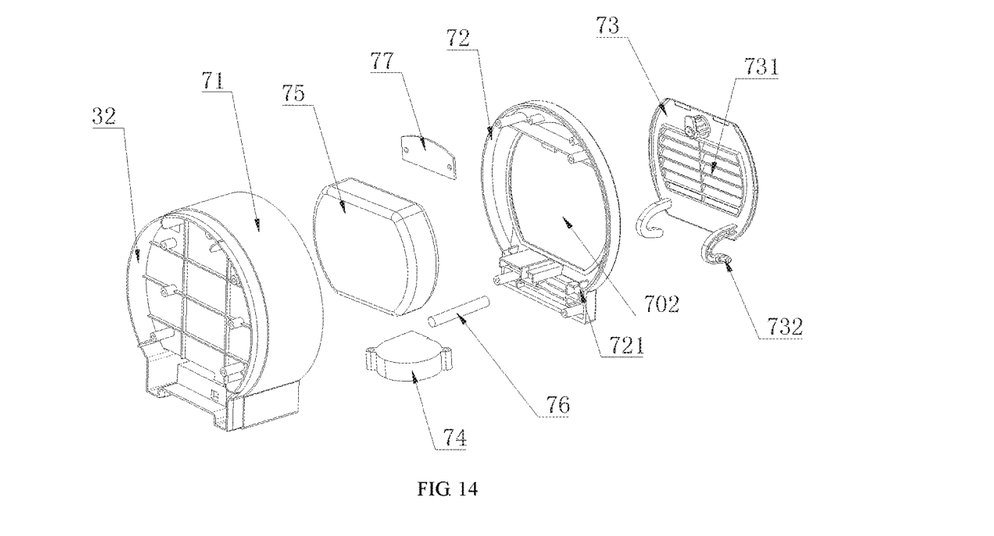
FIG. 14 is an exploded view of the perfume diffuser according to one embodiment of the present invention.

The perfume diffuser 70 further includes a fan 74 disposed on one side of the containing groove 701. When the fan 74 is powered on, circulation of air can be accelerated, then diffusion of the fragrance can be accelerated, and the room can be full of fragrance within a relatively short time. The user can set the power on time of the fan 74 according to demands so as to control the perfume diffuser 70 to diffuse fragrance at regular time. The invention is not limited thereto.

The perfume can be solid perfume or liquid perfume. If the perfume is solid perfume, the solid perfume can be directly positioned inside the containing groove 701. If the perfume is liquid perfume, the perfume diffuser 70 further includes a perfume bottle 75 and a volatilization stick 76. The perfume bottle 75 is filled with the liquid perfume, the perfume bottle 75 is positioned inside the containing groove 701, the volatilization stick 76 is inserted into the perfume bottle 75, and the fragrance can be volatilized out through the volatilization stick 76.

Figure 15:
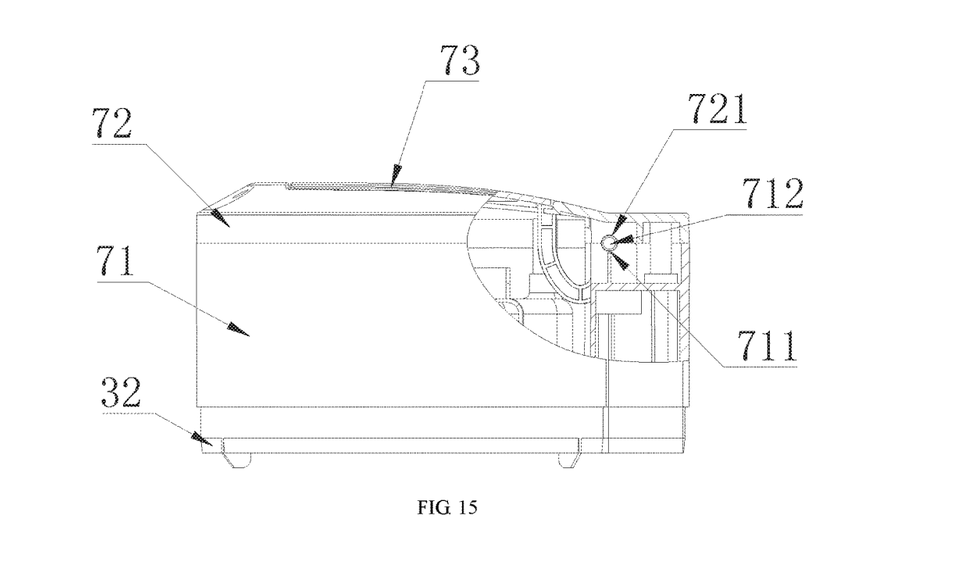
FIG. 15 is a partial sectional view of the perfume diffuser according to one embodiment of the present invention.

The window plate 73 has two rotating shafts 732. The window frame 72 has two first half grooves 721, the bottom cover 71 has two second half grooves, the two first half grooves 721 are respectively corresponding to the two second half grooves 711 to form two shaft holes 712, and the two rotating shafts 732 are rotatably inserted into the shaft holes 712, respectively. The rotating shafts 732 can rotate inside the shaft holes 712, so that the window plate 73 can be rotated relative to the window frame 72, the opening 702 can be opened, and the perfume in the containing groove 701 can be easily replaced.

The perfume diffuser 70 further includes a PCB 77 and an indicator light 78. The PCB 77, the indicator light 78 and the fan 74 are electrically connected, and the indicator light 78 is used for indicating the working state of the fan 74.

Corresponding to the hand dryer, the invention further provides a method for manufacturing the hand dryer, including:

Punching or extruding a plate so as to form a housing taking the shape of a hollow tube, and the housing having a first end and a second end.

Form a first end cover and a second end cover, a shape of the first end cover is the same as a shape of an end surface of the first end of the housing, and a shape of the second end cover is the same as a shape of an end surface of the second end of the housing.

Detachably connect the first end cover and the second end cover with two ends of the housing.

In the embodiment, the stainless steel plate is formed in a punching manner, so as to form the housing taking the shape of the hollow tube. The aluminum alloy material is extruded so as to form the housing taking the shape of the hollow tube.

The planar plate is punched or extruded to form the hollow tube, so that not only is the utilization rate of the plate high and formation procedures simple, but also only the bent part of the plate is deformed, other parts are not deformed, the plate has small surface deformation. The formed housing is smooth and free of damage in surface and needs no further machining, the machining procedures are greatly reduced, and the machining cost is lowered.

In conclusion, compared with the prior art, the hand dryer in the invention has following advantages.

The housing 1 of the hand dryer in the invention is designed into a hollow tube structure with two ends opened. the housing 1 of the hand dryer can be made of stainless steel plates with different surface appearances in a direct punching manner or made of an aluminum alloy material in an extrusion manner. The formation process is simple, the material utilization rate is high, and meanwhile as the formation process causes no damage, the original surface of the plate can be maintained after the product is formed, and the formed housing can be smooth and attractive and needs no extra polishing or spraying. The production efficiency is high, and the production cost is relatively low. Furthermore, the shape of the cross section of the first end cover 31 is the same as the shape of the end surface of the first end 13 of the housing 1, and the shape of the cross section of the second end cover 14 is the same as the shape of the end surface of the second end 14 of the housing 1. When the shape of the hand dryer needs to be changed, a user only needs to change the shapes of the housing 1 and the end cover 3, and other parts do not need to be redesigned, so that the product development cost can be greatly reduced, and the development period can be greatly shortened. Furthermore, the user can change the appearance of the hand dryer at will according to demands, so that the hand dryer is not only convenient to use, but also relatively low in use cost.

In addition, when being mounted, the hand dryer is fixed on the wall through a fixed connection with the mounting plate 4, the mounting buckle 5 and the groove plate 12. After being mounted, the mounting plate 4 and the mounting buckle 5 can be separated only by using special tools, so that the anti-theft effect of the hand dryer is greatly improved. As the baffle 6 is mounted, the sealed area 61 of the baffle 6 is disposed opposite to the air outlet 23, hands or other articles can be effectively prevented from stretching into the air outlet 23 to cause danger, furthermore noise generated when the blower is rotated inside the core can be conducted out through the air outlet 23 and can be reflected at the sealed area 61, and most noise can be conducted into the core 1 again, so that the operation noise of the hand dryer can be greatly reduced. Due to the noise reduction layer 100 disposed on the inner surface of the housing 1, the noise generated when the hand dryer is used can be further reduced. In addition, the hand dryer further includes the perfume diffuser 70, and due to the perfume diffuser 70, perform can be diffuse out to adjust the atmosphere of the room.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A hand dryer comprising:
a housing, taking a shape of a hollow tube with two ends opened and having a first end and a second end;
a core, disposed inside the housing, two ends of the core disposed correspondingly to two ends of the housing;
end covers, comprising a first end cover and a second end cover, the first end cover and the second end cover respectively detachably connected with the first end and the second end of the housing, the core fixed inside the housing, a shape of a cross section of the first end cover being the same as a shape of an end surface of the first end of the housing, and a shape of a cross section of the second end cover being the same as a shape of an end surface of the second end of the housing;
wherein the hand dryer comprises a mounting plate, a mounting buckle, and a groove plate, a side wall of the housing having a mounting groove concaving inwards to the housing, the mounting buckle and the groove plate being fixed on the mounting groove, and the mounting plate being fixedly connected with the mounting buckle and the groove plate;
wherein the mounting plate comprises a plate body, a connecting buckle, and a connecting plate, the connecting buckle and the connecting plate are disposed at two ends of the plate body, the connecting buckle is fixedly connected with the mounting buckle, and the connecting plate is connected with the groove plate;
wherein the mounting buckle comprises a mounting buckle bottom plate and a buckle plate, the mounting buckle bottom plate has a through hole, the buckle plate is disposed on one side of the through hole, and the buckle plate has a first connecting hole, a diameter of the connecting buckle is smaller than a diameter of the through hole, and the connecting buckle has a second connecting hole.

2. The hand dryer according to claim 1, further comprising a noise reduction layer disposed on an inner surface of the housing.

3. The hand dryer according to claim 1, wherein the core comprises a core housing, an air inlet and an air outlet, the air inlet and the air outlet are respectively disposed at two end surfaces of the core housing, the air outlet is disposed at an end surface close to the first end cover of the core housing, and the air inlet is disposed at an end surface close to the second end cover of the core housing.

4. The hand dryer according to claim 3, further comprising a baffle disposed on one side of the air outlet, the baffle having a sealed area and a grid area, and the sealed area disposed opposite to the air outlet.

5. The hand dryer according to claim 3, further comprising an air inlet grid, detachably disposed on one side away from the core of the first end cover.

6. The hand dryer according to claim 5, further comprising a filtering element, disposed between the air inlet grid and the first end cover.

7. The hand dryer according to claim 1, further comprising a display window, disposed at the first end cover, and being used for displaying a power on and operation state of the hand dryer.

8. The hand dryer according to claim 1, further comprising a perfume diffuser, disposed on one side of the second end cover.

9. The hand dryer according to claim 8, wherein the perfume diffuser includes a bottom cover, a window frame and a window plate, the bottom cover is disposed on one side of the second end cover, the window frame is mounted on one side of the bottom cover away from the second end cover, the bottom cover has a containing groove for containing perfume, the window frame has an opening, the window plate is rotatably mounted at the opening, and the window plate has a ventilation area.

10. The hand dryer according to claim 9, wherein the perfume diffuser further comprises a fan disposed on one side of the containing groove.

11. The hand dryer according to claim 9, wherein the perfume diffuser further comprises a perfume bottle and a volatilization stick, the perfume bottle is positioned inside the containing groove, and the volatilization stick is inserted into the perfume bottle.

12. The hand dryer according to claim 9, wherein the window plate has two rotating shafts, the window plate has two first half grooves, the bottom cover has two second half grooves, the two first half grooves are respectively corresponding to the two second half grooves to form two shaft holes, and two rotating shafts are rotatably inserted into the shaft holes.

\* \* \* \* \*